(12) United States Patent
Iwazaki

(10) Patent No.: US 6,271,382 B1
(45) Date of Patent: Aug. 7, 2001

(54) PROCESS FOR PRODUCING ORGANIC COMPOUND HAVING NITROXIDE FREE RADICAL

(75) Inventor: Katsuhiro Iwazaki, Osaka (JP)

(73) Assignee: Koei Chemical Co., Ltd., Osaka (JP)

( * ) Notice: Subject to any disclaimer, the term of this patent is extended or adjusted under 35 U.S.C. 154(b) by 0 days.

(21) Appl. No.: 09/623,084

(22) PCT Filed: Dec. 28, 1999

(86) PCT No.: PCT/JP99/07379
§ 371 Date: Aug. 28, 2000
§ 102(e) Date: Aug. 28, 2000

(87) PCT Pub. No.: WO00/39093
PCT Pub. Date: Jul. 6, 2000

(30) Foreign Application Priority Data

Dec. 28, 1998 (JP) .................................................. 10-374691

(51) Int. Cl.[7] .......................... C07D 211/94; C07D 207/46
(52) U.S. Cl. .......................... 546/184; 544/170; 544/383; 548/215; 548/542
(58) Field of Search .............................................. 546/184

(56) References Cited

U.S. PATENT DOCUMENTS

| | | | |
|---|---|---|---|
| 3,502,692 | * 3/1970 | Feldman et al. | ................. 260/326.3 |
| 5,218,116 | 6/1993 | Neri et al. . | |
| 5,436,345 | 7/1995 | Lewis et al. . | |
| 5,777,126 | 7/1998 | Pastor et al. . | |

FOREIGN PATENT DOCUMENTS

| | | |
|---|---|---|
| 6-247932 | 9/1994 | (JP) . |
| 8-3136 | 1/1996 | (JP) . |

* cited by examiner

Primary Examiner—Floyd D. Higel
Assistant Examiner—Sonya N. Wright
(74) Attorney, Agent, or Firm—Wenderoth, Lind & Ponack, L.L.P.

(57) ABSTRACT

An organic compound having a nitroxide free radial of the formula (2) is prepared by reacting a cyclic secondary amine having a steric hindrance of the formula (1) with a peroxide in the presence of at least 1 part by weight of an organic compound having a cyano group per 1 part by weight of the cyclic secondary amine having the steric hindrance. In the formulae (1) and (2), T is a methylene group, an ethylene group, an oxygen atom or a methyleneoxy group; R is an alkyl group, an aralkyl group, an aryl group, a cycloalkyl group, an alkoxy group, an acyl group an acyloxy group, an amino group, a hydroxyl group or a heterocyclic group; $R^1$, $R^2$, $R^3$ and $R^4$ are the same or different and each an alkyl group or an aryl group, or $R^1$ and $R^2$ and/or $R^3$ and $R^4$ together form a tetramethylene group or a pentamethylene group; and n is an integer of 0 to 6.

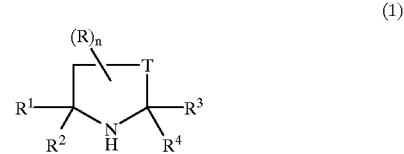

(1)

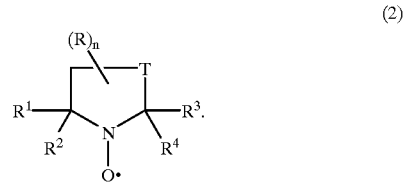

(2)

6 Claims, No Drawings

PROCESS FOR PRODUCING ORGANIC COMPOUND HAVING NITROXIDE FREE RADICAL

This application is a 371 application of PCT/JP99/07379 filed Dec. 28, 1999.

FIELD OF THE INVENTION

The present invention relates to a process for preparing an organic compound having a nitroxide free radial of the formula (2):

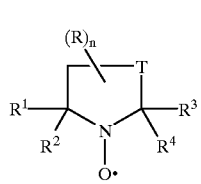

(2)

wherein T is a methylene group, an ethylene group, an oxygen atom or a methyleneoxy group; R is an alkyl group, an aralkyl group, an aryl group, a cycloalkyl group, an alkoxy group, an acyl group an acyloxy group, an amino group, a hydroxyl group or a heterocyclic group; $R^1$, $R^2$, $R^3$ and $R^4$ are the same or different and each an alkyl group or an aryl group, or $R^1$ and $R^2$ and/or $R^3$ and $R^4$ together form a tetramethylene group or a pentamethylene group; and n is an integer of 0 to 6. This compound will be referred to as the "nitroxide compound (2)".

The nitroxide compound (2) is useful as a spin label or a spin probe used in the ESR spectrum analysis, a polymerization inhibitor for unsaturated compound, or a stabilizer of organic polymers against thermal decomposition and photochemical decomposition.

BACKGROUND ART

It is known that an organic compound having a nitroxide free radical such as the nitroxide compound (2) is prepared by oxidizing a secondary amine having a steric hindrance with a peroxide. That is, the nitroxide compound (2) can be prepared by oxidizing a cyclic secondary amine having a steric hindrance of the formula (1):

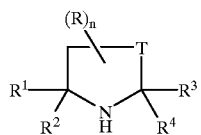

(1)

wherein T, R, $R^1$, $R^2$, $R^3$, $R^4$ and n are the same as defined above with a peroxide.

However, when 2,2,6,6-tetramethylpiperidine is used as a cyclic secondary amine (1) and it is oxidized to obtain 2,2,6,6-tetramethylpiperidine-N-oxyl, industrially satisfactory results are not attained, for example, the yield of the desired product is low as understood from the result of Comparative Examples described below, and the reaction time is long.

DISCLOSURE OF THE INVENTION

One object of the present invention is to provide a process for preparing the nitroxide compound (2) by oxidizing the cyclic secondary amine (1) with a peroxide at a high yield in a short reaction time.

The present inventors have made extensive study to solve the above problems. As a result, it has been found that the nitroxide compound (2) can be obtained at a high yield in a short reaction time, when the cyclic secondary amine (1) is reacted with the peroxide in the presence of at least 1 wt. part of an organic compound having a cyano group per 1 wt. part of the cyclic secondary amine (1), and the present invention has been completed.

Accordingly, the present invention provides a process for preparing the nitroxide compound (2) comprising the step of reacting a cyclic secondary amine of the formula (1):

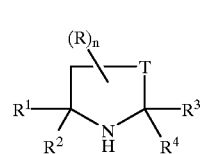

(1)

with a peroxide in the presence of at least 1 wt. part of an organic compound having acyano group per 1 wt. part of the cyclic secondary amine (1).

EMBODIMENTS FOR CARRYING OUT THE INVENTION

The present invention will be explained in detail.

In the above formula (1), which represents the cyclic secondary amine used in the process of the present invention, T is a methylene group, an ethylene group, an oxygen atom or a methyleneoxy group; R is an alkyl group, an aralkyl group, an aryl group, a cycloalkyl group, an alkoxy group, an acyl group an acyloxy group, an amino group, a hydroxyl group or a heterocyclic group; $R^1$, $R^2$, $R^3$ and $R^4$ are the same or different and each an alkyl group or an aryl group, or $R^1$ and $R^2$ and/or $R^3$ and $R^4$ together form a tetramethylene group or a pentamethylene group; and n is an integer of 0 to 6.

The alkyl group represented by R may be a linear or branched alkyl group having 1 to 6 carbon atoms. Specific examples of the alkyl group include a methyl group, an ethyl group, a n-propyl group, an isopropyl group, a n-butyl group, an isobutyl group, a n-pentyl group, an isopentyl group, a neopentyl group, a n-hexyl group, a 2-methylpentyl group, a 3-methylpentyl group, a neohexyl group, etc.

The aralkyl group may be an aralkyl group having 7 to 15 carbon atoms. Specific examples of the aralkyl group include a benzyl group, a phenethyl group, a phenylpropyl group, a benzhydryl group, etc.

Specific examples of the aryl group include a phenyl group, a tolyl group, a xylyl group, a naphthyl group, etc.

The cycloalkyl group may be a cycloalkyl group having 3 to 8 carbon atoms. Specific examples of the cycloalkyl group include a cyclopropyl group, a cyclobutyl group, a cyclopentyl group, a cyclohexyl group, a cycloheptyl group, a cyclooctyl group, etc.

Specific examples of the alkoxy group include alkyloxy groups (e.g. a methoxy group, an ethoxy group, a propoxy group, etc.), and aralkyloxy groups (e.g. a benzyloxy group, etc.) Specific examples of the acyl group include linear or branched lower alkanoyl groups having 1 to 6 carbon atoms (e.g. a formyl group, an acetyl group, a propionyl group, a butyryl group, a valeryl group, a pivaloyl group, a pentanoyl group, etc.) and aroyl groups (e.g. a benzoyl group, a toluoyl group, a xyloyl group, a naphthoyl group, etc.)

Specific examples of the acyloxy group include alkanoyloxy gropus (e.g. an acetoxy group, a propionyloxy group, etc.) and aroyloxy groups (e.g. a benzoyloxy group, etc.)

Specific examples of the heterocyclic group include a thienyl group, a pyrrolyl group, a pyranyl group, a thiopyranyl group, a pyridyl group, a thiazolyl group, an imidazolinyl group, a pyrimidinyl group, a triazinyl group, an indolyl group, a quinolyl group, a purinyl group, a benzothiazolyl group, etc.

R in the formula substitutes a hydrogen atom on the ring of the cyclic secondary amine (1)

Examples of the alkyl and aryl groups represented by $R^1$, $R^2$, $R^3$ and $R^4$ may be the same as those exemplified in connection with R. Preferably, $R^1$, $R^2$, $R^3$ and $R^4$ are methyl groups.

Specific examples of the cyclic secondary amine (1) include 2,2,5,5-tetramethylpyrrolidine; derivatives of 2,2,5,5-tetramethylpyrrolidine which have a substituent such as an alkoxy group (e.g. a methoxy group, an ethoxy group, a propoxy group, abenzyloxygroup, etc.), anacyloxygroup (e.g. anacetoxy group, a propionyloxy group, a benzoyloxy group, etc.) or a hydroxyl group on the 3-position of 2,2,5,5-tetramethylpyrrolidine; 2,2,6,6-tetramethylpiperidine; derivatives of 2,2,6,6-tetramethylpiperidine which have a substituent such as an alkoxy group (e.g. a methoxy group, an ethoxy group, a propoxy group, a benzyloxy group, etc.), an acyloxy group (e.g. an acetoxy group, a propionyloxy group, a benzoyloxy group, etc.) or a hydroxyl group on the 4-position of 2,2,6,6-tetramethylpiperidine; derivatives of 4,4-dimethyloxazolidine such as 2,2,4,4-tetramethyloxazolidine, 2,4,4-trimethyl-2-phenyloxazolidine, 4-aza-3,3-dimethyl-1-oxaspiro [4.5] decane, etc.; 3,3,5,5-tetramethylmorpholine; derivatives of 3,3,5,5-tetramethylmorpholine which have a substituent such as an alkyl group (e.g. a methyl group, etc.) on the 2-position of 3,3,5,5-tetramethylmorpholine. The cyclic secondary amine (1) may not be limited to the above exemplified compounds.

According to the process of the present invention, the nitroxide compound (2) corresponding to the above cyclic secondary amine (1) can be obtained. For example, 2,2,5,5-tetramethylpyrrolidine-N-oxyl and its derivatives are prepared from 2,2,5,5-tetramethylpyrrolidine and its derivatives, 2,2,6,6-tetramethylpiperizine-N-oxyl and its derivatives are prepared from 2,2,6,6-tetramethylpiperizine and its derivatives, 4,4-dimethyloxazolidine-N-oxyl derivatives are prepared from 4,4-dimethyloxazolidine derivatives, and 3,3,5,5-tetramethylmorpholine-N-oxyl and its derivatives are prepared from 3,3,5,5-tetramethylmorpholine and its derivatives.

As the peroxide used in the process of the present invention, hydrogen peroxide and any organic peroxide such as hydroperoxide and peracids may be used. Among them, hydrogen peroxide is preferable from the viewpoint of costs and the reduction of the amount of wastes.

When hydrogen peroxide is used, a 5–70 wt. % aqueous solution, preferably a 20–50 wt. % aqueous solution of hydrogen peroxide is used. The amount of hydrogen peroxide is at least 1.5 moles, preferably from 1.6 to 3.5 moles per 1 mole of the cyclic secondary amine (1).

In the process of the present invention, the reaction is carried out in the presence of at least 1 wt. parts, preferably 1.5 to 50 wt. parts, more preferably 2 to 30 wt. parts of an organic compound having a cyano group per 1 wt. parts of the cyclic secondary amine (1). More preferably, the reaction is carried out in the presence of at least 1.5 moles, preferably 2 to 50 moles of the organic compound having the cyano group per 1 mole of the cyclic secondary amine group (1) in the above weight parts range.

The organic compound having the cyano group is not limited except those having a polymerizable double bond in the molecule such as acrylonitrile. Preferable examples of the organic compound having the cyano group include aliphatic nitrites (e.g. acetonitrile, propionitrile, butyronitrile, valeronitrile, capronitrile, etc.) and aromatic nitrites (e.g. benzonitrile, tolunitrile, etc.)

When hydrogen peroxide is used in the form of an aqueous solution, the organic compound having the cyano group is preferably a water-soluble one, particularly preferably an acetonitrile and/or propionitrile.

The process of the present invention may be carried out in a solvent. The solvent is suitably selected depending on the kinds of the cyclic secondary amine (1), the organic compound having the cyano group and the nitroxide compound (2), and preferably selected from solvents which are good solvents for the cyclic secondary amine (1) and the nitroxide compound (2), and miscible with the organic compound having the cyano group. Examples of the solvent include water, alcohols (e.g. methanol, ethanol, propanol, butanol, isopropanol, etc.), aromatic hydrocarbons (e.g. benzene, toluene, xylene, mesitylene, etc.), ethers (e.g. diethyl ether, diisopropyl ether, tetrahydrofuran, etc.) and so on. Preferred solvents are those which are not oxidized with the nitroxide compound (2), for example, water, the aromatic hydrocarbons, the ethers, etc.

The solvent may not be used when the amount of the organic compound having the cyano group is at least 2.5 wt. parts, preferably at least 3 wt. parts per 1 wt. parts of the cyclic secondary amine (1), since the organic compound having the cyano group serves as a solvent in the process of the present invention.

A catalyst may be used in the process of the present invention. The catalyst may be one that is used in a known process for preparing a compound having a nitroxide free radical by oxidizing a corresponding secondary amine having a steric hindrance with a peroxide. Preferred examples of the catalyst are compounds comprising metal elements of the 6 Group of the 18 Groups Periodic Table, for example, tungsten, molybdenum, etc. Specific examples of the tungsten compound include tungstic acid, phosphortungstic acid, paratungstic acid, and their alkali metal salts (e.g. sodium salts, potassium salts) or ammonium salts. Specific examples of the molybdenum compounds include molybdic acid, molybdenum oxide, molybdenum carbonyl and their alkali metal salts (e.g. sodium salts, potassium salts) or ammonium salts). Specific examples include ammonium paratungstate, sodium tungstate, phosphortungstic acid, sodium molybdate, molybdenum trioxide, molybdenum hexacarbonyl, etc.

The amount of the catalyst is usually from 0.001 to 0.1 wt. %, preferably from 0.01 to 0.05 wt. % of the weight of the cyclic secondary amine (1).

The procedure of the process according to the present invention will be explained. For example, the peroxide is added to the mixture of the cyclic secondary amine (1) and the organic compound having the cyano group while stirring to react the cyclic secondary amine and the peroxide.

The reaction temperature is usually from 0 to 75° C., preferably from 40 to 65° C.

The nitroxide compound (2) can be prepared at ahigher yield by the above manner in which the reaction proceeds while the peroxide is added, although the cyclic secondary amine (1), the organic compound having the cyano group and the peroxide are mixed and reacted at the above temperature while stirring.

The addition time of the peroxide is not limited, and usually from 1 to 10 hours, preferably from 3 to 6 hours. After the addition of the peroxide, the reaction mixture is maintained at the above temperature for 1 to 10 hours to complete the reaction.

After the completion of the reaction, the nitroxide compound (2) may be isolated from the reaction mixture by a suitable combination of unit procedures such as concentration, extraction, distillation, recrystallization, etc.

EXAMPLES

The present invention will be illustrated by the Examples, which do not limit the present invention in any way.

Example 1

In a 100 ml reactor, 2,2,6,6-tetramethylpiperidine (4.3 g), acetonitrile (38.6 g) and ammonium paratungstate (0.21 g) were charged, and 35% aqueous hydrogen peroxide (8.8 g) was dropwise added to the mixture over 3 hours while stirring and maintaining the temperature at 50 to 51° C., followed by further reaction while stirring at the same temperature for 3 hours. After the completion of the reaction, the reaction mixture was analyzed with gas chromatography. The yield of 2,2,6,6-tetramethylpiperidine-1-oxyl was 93.5% (based on 2,2,6,6-tetramethylpiperidine).

Example 2

A reaction was carried out in the same manner as in Example 1 except that a half of acetonitrile (19.3 g) was replaced by tetrahydrofuran (19.3 g). As a result, the yield of 2,2,6,6-tetramethylpiperidine-1-oxyl was 92.3% (based on 2,2,6,6-tetramethylpiperidine).

Example 3

In a 100 ml reactor, 2,2,6,6-tetramethylpiperidine (8.5 g), acetonitrile (25.5 g) and ammonium paratungstate (0.42 g) were charged, and 35% aqueous hydrogen peroxide (17.5 g) was dropwise added to the mixture over 3 hours while stirring and maintaining the temperature at 50 to 51° C., followed by further reaction while stirring at the same temperature for 3 hours. After the completion of the reaction, the reaction mixture was analyzed with gas chromatography. The yield of 2,2,6,6-tetramethylpiperidine-1-oxyl was 90.1% (based on 2,2,6,6-tetramethylpiperidine).

Example 4

In a 100 ml reactor, 2,2,6,6-tetramethylpiperidine (8.5 g), acetonitrile (12.8 g), methanol (12.8 g) and ammonium paratungstate (0.42 g) were charged, and 35% aqueous hydrogen peroxide (17.5 g) was dropwise added to the mixture over 3 hours while stirring and maintaining the temperature at 50 to 51° C., followed by further reaction while stirring at the same temperature for 3 hours. After the completion of the reaction, the reaction mixture was analyzed with gas chromatography. The yield of 2,2,6,6-tetramethylpiperidine-1-oxyl was 71.2% (based on 2,2,6,6-tetramethylpiperidine).

Example 5

A reaction was carried out in the same manner as in Example 3 except that no ammonium paratungstate was used. As a result, the yield of 2,2,6,6-tetramethylpiperidine-1-oxyl was 94.4% (based on 2,2,6,6-tetramethylpiperidine).

Example 6

A reaction was carried out in the same manner as in Example 5 except that the amount of hydrogen peroxide was changed to 11.7 g and the addition time of hydrogen peroxide was changed to 2 hours. As a result, the yield of 2,2,6,6-tetramethylpiperidine-1-oxyl was 93.1% (based on 2,2,6,6-tetramethylpiperidine).

Comparative Example 1

A reaction was carried out in the same manner as in Example 1 except that the amount of acetonitrile was changed to 2.5 g and methanol (36.1 g) was used. As a result, the yield of 2,2,6,6-tetramethylpiperidine-1-oxyl was 52.0% (based on 2,2,6,6-tetramethylpiperidine).

Comparative Example 2

A reaction was carried out in the same manner as in Example 1 except that tetrahydrofuran (38.6 g) was used in place of acetonitrile (38.6 g), and the reaction was continued for 10 hours while stirring after the completion of the addition of hydrogen peroxide. As a result, the yield of 2,2,6,6-tetramethylpiperidine-1-oxyl was 38.5% (based on 2,2,6,6-tetramethylpiperidine).

The conditions and the results of Examples and Comparative Examples are summarized in the following Table.

TABLE 1

|  | TMPPR g (mole) | 35% $H_2O_2$ g (mole) | $CH_3CN$ g (mole) | Solvent g | Catalyst g | Yield % |
|---|---|---|---|---|---|---|
| Ex. 1 | 4.3(0.03) | 8.8(0.09) | 38.6(0.94) | 0 | 0.21 | 93.5 |
| C. Ex. 1 | 4.3(0.03) | 8.8(0.09) | 2.5(0.47) | $CH_3OH$ 36.1 | 0.21 | 52.0 |
| Ex. 2 | 4.3(0.03) | 8.8(0.09) | 19.3(0.47) | THF 19.3 | 0.21 | 92.3 |
| C. Ex. 2 | 4.3(0.03) | 8.8(0.09) | 0 | THF 38.6 | 0.21 | 38.5 |
| Ex. 3 | 8.5(0.06) | 17.5(0.18) | 25.5(0.62) | 0 | 0.42 | 90.1 |
| Ex. 4 | 8.5(0.06) | 17.5(0.18) | 12.8(0.31) | $CH_3OH$ 12.8 | 0.42 | 71.2 |
| Ex. 5 | 8.5(0.06) | 17.5(0.18) | 25.5(0.62) | 0 | 0 | 94.4 |
| Ex. 6 | 8.5(0.06) | 11.7(0.12) | 25.5(0.62) | 0 | 0 | 93.1 |

What is claimed is:

1. A process for preparing an organic compound having a nitroxide free radical of the formula (2):

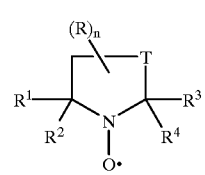

(2)

wherein T is a methylene group, an ethylene group, an oxygen atom or a methyleneoxy group; R is an alkyl group, an aralkyl group, an aryl group, a cycloalkyl group, an alkoxy group, an acyl group an acyloxy group, an amino group, a hydroxyl group or a heterocyclic group; $R^1$, $R^2$, $R^3$ and $R^4$ are the same or different and each is an alkyl group or an aryl group, or $R^1$ and $R^2$ and/or $R^3$ and $R^4$ together form a tetramethylene group or a pentamethylene group; and n is an integer of 0 to 6, comprising the step of reacting a cyclic secondary amine having a steric hindrance of the formula (1):

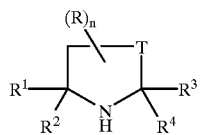

(1)

wherein T, R, $R^1$, $R^2$, $R^3$, $R^4$ and n are the same as defined above with a peroxide in the presence of at least 1 part by weight of an organic compound having a cyano group per 1 part by weight of the cyclic secondary amine (1).

2. The process according to claim 1, wherein the reaction is carried out in the presence of a catalyst.

3. The process according to claim 2, wherein said catalyst is a compound comprising a metal element of the 6 Group of the 18 Groups Periodic Table.

4. The process according to claim 1, wherein said peroxide is hydrogen peroxide.

5. The process according to claim 2, wherein said peroxide is hydrogen peroxide.

6. The process according to claim 3, wherein said peroxide is hydrogen peroxide.

* * * * *